May 7, 1974 MARIE-LOUIS MEILLAND Plant Pat. 3,546
ROSE PLANT
Filed Aug. 18, 1972
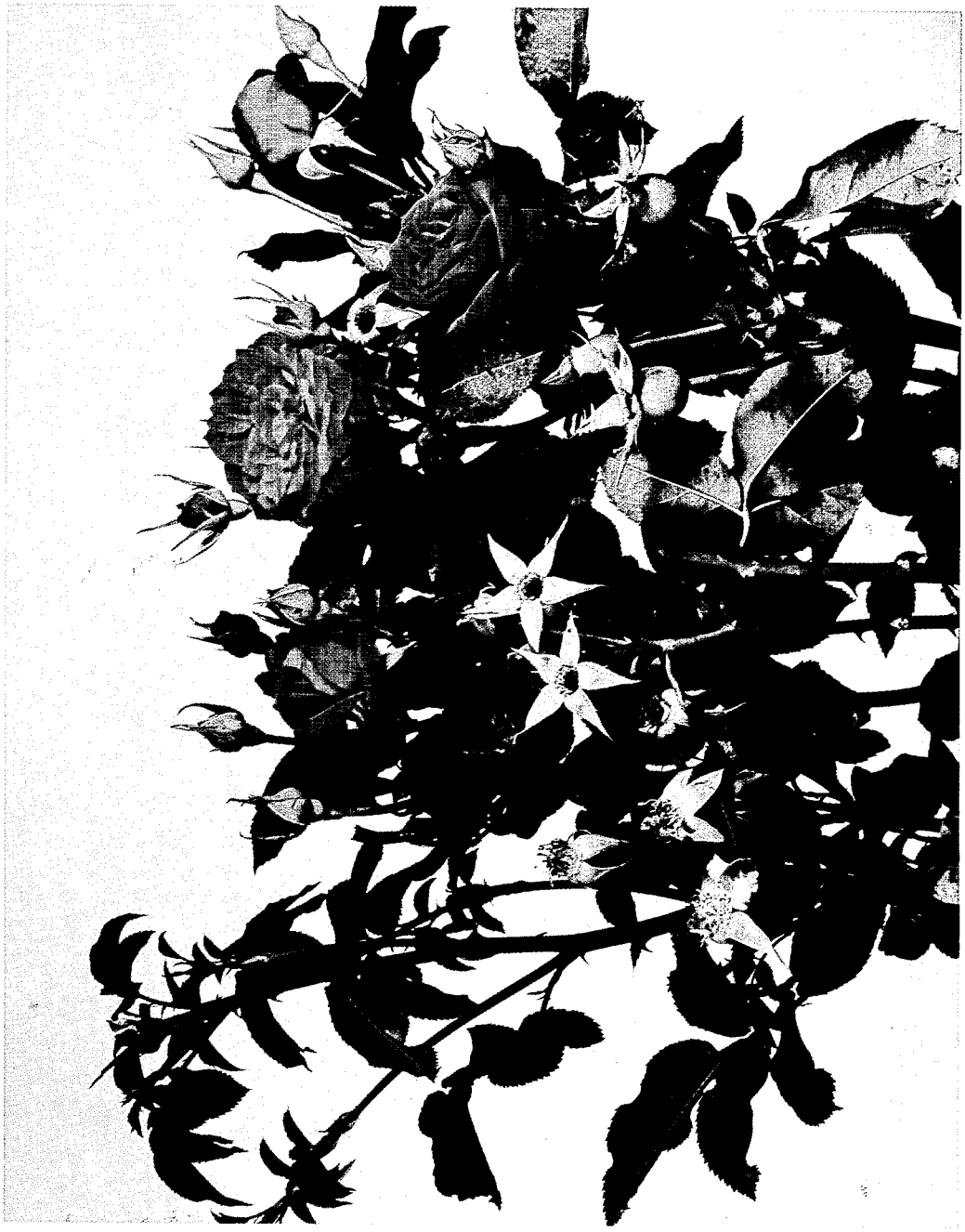

United States Patent Office

Plant Pat. 3,546
Patented May 7, 1974

3,546

ROSE PLANT (PAT NIXON)

Marie-Louis Meilland, Cap d'Antibes, France, assignor to C. H. Stuart & Company, Inc., Newark, N.Y.

Filed Aug. 18, 1972, Ser. No. 281,929
Int. Cl. A01h *5/00*
U.S. Cl. Plt.—28 1 Claim

ABSTRACT OF THE DISCLOSURE

A rose plant of the floribunda class originated by crossing Tamango (U.S. Plant Pat. No. 2,857) with an unnamed and unpatented rose seedling which resulted from a crossing of Fire King (U.S. Plant Pat. No. 1,758) with Banzai (U.S. Plant Pat. No. 2,142).

SUMMARY OF THE INVENTION

My invention relates to a new and distinct variety of rose plant of the floribunda class which was originated by me by crossing the rose known as Tamango (U.S. Plant Pat. No. 2,857) with an unnamed and unpatented rose seedling which resulted from a cross of Fire King (U.S. Plant Pat. No. 1,758) with Banzai (U.S. Plant Pat. No. 2,142). Tamango was the seed parent and the unnamed and unpatented seedling was the pollen parent.

As the result of this crossing, I have produced a new and useful rose variety which is distinguished from its parents, and all rose varieties of which I am aware, as evidenced by the following unique combination of characteristics which are outstanding therein:

(1) A bushy, vigorous, much branched plant of average height for the class;

(2) Flowers of good form in bud and when fully developed with up to 50 velvety petals of uniform, attractive red color;

(3) Continuous, abundant flower production for garden and landscape decoration as well as cut flowers for indoor use;

(4) Flowers produced singly on stems for cutting and in irregular clusters of several to the stem giving an attractive flowering effect;

(5) Abundant, medium sized leaves of moderately glossy and smooth, moderately leathery texture with above normal resistance to disease for roses of this class; and (6) Winter-hardiness above normal for garden roses of the floribunda class.

My new variety is distinguished from its seed parent by deeper, more uniform red color of the flower and with the flower newly opened averaging at least 10 more petals, so the reproductive parts of the flower are less conspicuous. New shoots and new leaves of my new variety are of more mahogany-red (general color term) than the seed parent with mature foliage a deeper, bluer green (general color term) than the seed parent. When compared to the pollen parent, my new rose has more vigorous, branched and taller growth characteristics with flowers of smaller size and much less tendency to have white streaks in the petals.

Reproduction of my new variety by asexual budding of several generations has been accomplished in France and at West Grove, Pennsylvania, and at McFarland, California. The unique combination of chracteristics of my rose have held true and consistent through these successive asexual propagations.

BRIEF DESCRIPTION OF DRAWING

The accompanying drawing shows typical specimens of the vegetative growth and the flowers and reproductive parts of my new invention in various stages of development and is depicted in color as nearly true as it is reasonably possible to have a color illustration of this character.

DETAILED DESCRIPTION OF DISCLOSURE

The following is a detailed description of the new variety with color terminology in accordance with the Colour Chart of the Royal Horticultural Society, London, England, except where general color terms of ordinary dictionary significance are obvious:

Type: Hardy; bush, outdoor; seedling; garden decoration.
Class: Floribunda.
Propagation: It does hold its distinguishing characteristics through succeeding propagations by budding.

*Flower*

Locality where grown: West Grove, Pennsylvania
Flowers borne: Singly and several to stem; in irregular cluster; on medium long stems.
Quantity of bloom: Abundant outdoors.
Continuity: Continuous.
Fragrance: Slight; tea.

Bud: Peduncle: Medium; bending, medium erect; light green 144B; almost smooth; few hairs; green.
*Before calyx breaks.*—Size: Small. Form: Pointed with a conspicuous neck; with foliaceous appendages on the surface of the bud; with slender foliaceous parts extending beyond the tip of the bud equal to ½ or more of its length.
*As calyx breaks.*—Color: 53A.
*As first petal opens.*—Size: Small to medium. Form: Short globular. Color: Outside: 53C, inside: 46A. Opening: It does open up well.

Bloom:
*Size when fully open.*—Medium, 2½ to 3 inches.
*Petalage.*—Double; from 35 to 50 petals; arranged regularly.
*Form.*—Cupped at first; becoming flat; petals remaining at first loosely rolled outward; becoming later at maturity loosely flat rolled outward.

Petals: Thick; with inside velvety; outside satiny.
*Shape.*—Outer: Round; with 1 notch. Intermediate: Obovate; with apex flat. Inner: Obovate; with apex flat.

This description of a newly opened flower was made from a rose grown outdoors.
*Color.*—Outer petal: Outside surface: 53C; inside surface: 46C. Intermediate petal: Outside surface: 53C; inside surface: 46C. Inner petal: Outside surface: 53C; inside surface: 46C.

This description was made from a rose that was open for three days outdoors.
*Color.*—Outer petal: Outside surface: 53C; inside surface: 46C. Inner petal: outside surface: 53D; inside surface: 46C.
*General color effect.*—Newly opened flower: 46B. Three days open: 46B at the outer edge shaded to 46C at the center.
*Behavior.*—Drop off cleanly.
*Flower longevity.*—On bush in garden 3 to 4 days in early September; cut roses grown outdoors kept at living room temperatures 3 to 4 days in early September.

*Reproductive organs*

Stamens: Medium; arranged regularly about pistils.
Filaments: Most with anthers; medium long.
*Color.*—48D.
Anthers: Open at various times; small. Color: 15C. Occasionally an anther fused with a petaloid.
Pollen: Moderate; gold.
Pistils: Many.
Styles: Even: medium long; very thin; bunched columnar.
Stigma: White.

Ovaries: All enclosed in receptacle.
Hips: Medium globular with inconspicuous neck; moderately hairy; walls thick fleshy; green.
Sepals: Permanent; long, straight spear shaped.
Seeds: Medium number; medium size.

*Plant*

Foliage:

*Leaves.*—Compound of 3 or 5; abundant; medium size; moderately leathery.

*Leaflets.*—Shape: With apex acute, base round, simply serrate.

*Color.*—Mature—Upper surface: 131B; under surface: 147B. Young—Upper surface: 135A; under surface: 178A.

*Rachis (the supporting stem of the compound leaf).*—Medium. Upper side: Smooth, grooved. Under side: Sparsely prickly, thorny.

*Stipules.*—Moderately long; medium wide; with medium points; turning out at an angle of more than 45°, recurved toward the stem.

*Disease.*—Resistance comparable to the average variety growing under the same cultural conditions.

Growth:

*Habit.*—Bushy, much branched.

*Growth.*—Vigorous.

*Canes.*—Medium.

*Main stems.*—Dull. Color: 146A. Prickles: several; color: 178A. Hairs: None.

*Branches.*—Dull. Color: 146A. Prickles: several; color: 178A. Hairs: None.

*Branches.*—Dull. Color: 146A. Prickles: several; color: 178B; Hairs: None.

*New shoots.*—Dull. Color: 178A. Prickles: several; color: 178A. Hairs: None.

I claim:

1. A new and distinct variety of rose plant of the floribunda class, substantially as herein shown and described, characterized particularly as to novelty by the unique combination of bushy, vigorous, much branched plant of medium height, flowers with petals arranged in regular and pleasing form in all stages of maturity and with uniform red color from one petal to the next regardless of the maturity of the flower; with these flowers borne continuously and abundantly, singly and in irregular clusters, several to the stem, with abundant foliage moderately glossy, smooth with moderately leathery texture with resistance to disease comparable to the average of roses of the floribunda class, and with winter hardiness more than typical for the class.

No references cited.

ROBERT E. BAGWILL, Primary Examiner